(12) United States Patent
Nashimoto et al.

(10) Patent No.: US 9,617,538 B2
(45) Date of Patent: Apr. 11, 2017

(54) HEPTAMER-TYPE SMALL GUIDE NUCLEIC ACIDS INDUCING APOPTOSIS OF HUMAN LEUKEMIA CELLS

(75) Inventors: Masayuki Nashimoto, Nigata (JP); Masuhiro Takahashi, Niigata (JP); Miwako Narita, Niigata (JP); Tetsuo Yoshida, Tokyo (JP); Tatsuya Miyazawa, Tokyo (JP)

(73) Assignees: NIIGATA UNIVERSITY OF PHARMACY AND APPLIED LIFE SCIENCE, Niigata (JP); NIIGATA UNIVERSITY, Niigata (JP)

( * ) Notice: Subject to any disclaimer, the term of this patent is extended or adjusted under 35 U.S.C. 154(b) by 0 days.

(21) Appl. No.: 14/241,580

(22) PCT Filed: Aug. 24, 2012

(86) PCT No.: PCT/JP2012/071503
§ 371 (c)(1),
(2), (4) Date: Mar. 11, 2014

(87) PCT Pub. No.: WO2013/031704
PCT Pub. Date: Mar. 7, 2013

(65) Prior Publication Data
US 2015/0025232 A1    Jan. 22, 2015

(30) Foreign Application Priority Data

Aug. 29, 2011 (JP) .................. 2011-185594

(51) Int. Cl.
*C07H 21/02* (2006.01)
*C12N 15/113* (2010.01)
*A61K 31/7105* (2006.01)

(52) U.S. Cl.
CPC ........ *C12N 15/113* (2013.01); *A61K 31/7105* (2013.01); *C12N 2310/12* (2013.01)

(58) Field of Classification Search
None
See application file for complete search history.

(56) References Cited

U.S. PATENT DOCUMENTS

| 6,500,615 B1 | 12/2002 | Schmidt et al. |
| 6,582,908 B2 * | 6/2003 | Fodor et al. ............ 506/9 |
| 2005/0255487 A1 * | 11/2005 | Khvorova et al. ........... 435/6 |
| 2006/0185027 A1 * | 8/2006 | Bartel et al. .............. 800/14 |
| 2007/0015189 A1 * | 1/2007 | Biro ....................... 435/6 |

FOREIGN PATENT DOCUMENTS

| JP | 2001-501479 | 2/2001 |
| WO | WO 95/31434 | * 11/1995 |
| WO | 2004/024314 | 3/2004 |
| WO | WO 2009/043353 | * 4/2009 |

OTHER PUBLICATIONS

GenBank NM_001202.2 (2007).*
GenBank NM_001442.1 (2008).*
GenBank NM_004557.2 (2004).*
GenBank NM_020529.1 (2008).*
Krutzfeld et al (Nature 438(1): 685-689).*
Takahisa et al., "tRNase Z to TRUE gene silencing", Kagaku to Seibutsu, Mar. 2011, vol. 49, No. 3, pp. 150-152.
Elbarbary et al., "Inhibition of vascular endothelial growth factor expression by TRUE gene silencing", Biochemical and Biophysical Research Communications, 2009, vol. 379, pp. 924-927.
Nakashima et al., "Gene silencing by the tRNA maturase tRNase $Z^L$ under the direction of small-guide RNA", Gene Therapy, 2007, vol. 14, pp. 78-85.
Tamura et al., "Intracellular mRNA cleavage by 3' tRNase under the direction of 2'-O-methyl RNA heptamers" Nucleic Acids Research, 2003, vol. 31, No. 15, pp. 4354-4360.
International Search Report issued Sep. 25, 2012 in International (PCT) Application No. PCT/JP2012/071503.
M. Takahashi et al., "TRUE Gene Silencing: Finding Blood Cancer Therapeutic sgRNAs", The 16$^{th}$ Annual Meeting of the RNA Society and the 13$^{th}$ Annual Meeting of the RNA Society of Japan, RNA 2011, pp. 84 and 167, Jun. 14-16, 2011.
T. Sano et al., "Expanding the Utility of Heptamer-Type sgRNA for TRUE Gene Silencing", Biochemical and Biophysical Research Communications, vol. 416, pp. 427-432, Dec. 16, 2011.

* cited by examiner

*Primary Examiner* — Richard Schnizer
(74) *Attorney, Agent, or Firm* — Wenderoth, Lind & Ponack, L.L.P.

(57) ABSTRACT

There is provided a heptamer-type small guide nucleic acid that comprises any of the 7-base sequences of SEQ ID NOS: 1 to 15, and induces apoptosis of human leukemia cells. A leukemia therapeutic agent containing the heptamer-type small guide nucleic acid as an active ingredient is also provided. The novel heptamer-type sg nucleic acid can induce apoptosis of human leukemia cells.

2 Claims, 3 Drawing Sheets

Hep2(Bcl-2)

*Fig. 5*

Hep1(MYC)

*Fig. 6*

Hep8(FGFR3)

*Fig. 7*

Hep9(FGFR3)

*Fig. 8*

Hep6(PRAME)

*Fig. 9*

Hep7(WT1)

HEPTAMER-TYPE SMALL GUIDE NUCLEIC ACIDS INDUCING APOPTOSIS OF HUMAN LEUKEMIA CELLS

TECHNICAL FIELD

The present invention relates to heptamer-type small guide nucleic acids which effectively induce apoptosis of human leukemia cells.

BACKGROUND

The inventors of this application have developed a novel technology for suppressing gene expression termed TRUE (tRNase $Z^L$-utilizing efficacious gene silencing) gene silencing (PTL 1, NPL 1-4). tRNase $Z^L$ is a long form of tRNA 3' processing endoribonuclease (tRNase Z, or 3' tRNase), which can remove a 3' trailer from precursor tRNA (NPL 5, 6). TRUE gene silencing is based on an additional unique enzymatic property of mammalian tRNase $Z^L$, which is that it can cleave any target RNA at any desired site by recognizing a pre-tRNA-like or micro-pre-tRNA-like complex formed between the target RNA and artificial small guide nucleic acids (NPL 7-13). Small guide nucleic acid (especially, small guide RNA) is divided into four groups, 5'-half-tRNA (NFL 8), 12-16-nt linear RNA (NPL 13), heptamer-type RNA (NPL 9), and hook-type RNA (NPL 12).

The inventors have demonstrated the efficacy of TRUE gene silencing in various mammalian cells by introducing small guide nucleic acids targeting various mRNAs either as their expression plasmids or as 2'-O-methyl RNAs (NPL 1-4) (hereinafter, the small guide nucleic acid may be referred as "sg nucleic acid"). For example, the HIV-1 expression in Jurkat cells was almost completely suppressed by a 5'-half-tRNA-type sgRNA up to 18 days (NPL 2), and a luciferase gene expression in the mouse livers was inhibited by a heptamer-type sgRNA (NPL 3). Furthermore, it have been shown that the efficacy of TRUE gene silencing can become comparable to that of the RNA interference (RNAi) (NPL 3, 14) and can surpass it in some cases (NPL 4).

Recently, the inventors have found that tRNase $Z^L$ exists in the cytosol as well as in the nuclei and that 5'-half-tRNA, which is exactly what they have been using as sg nucleic acid, exists in the cytoplasm (NPL 15). The inventors have also shown that human cytosolic tRNase $Z^L$ modulates gene expression by cleaving mRNA under the direction of 5'-half-tRNA and that the PPMIF mRNA is one of the genuine targets of tRNase $Z^L$ (NPL 15). Furthermore, the inventors have demonstrated that a subset of human miRNAs including miR-103 can work as hook-type sg nucleic acid and can downregulate gene expression through directing mRNA cleavage by cytosolic tRNase $Z^L$ (NPL 16). It is obvious that TRUE gene silencing functions on the basis of the newly unveiled physiological role of cytosolic tRNase $Z^L$ directed by cellular small noncoding RNAs.

One of the final destinations of TRUE gene silencing is to generate cancer therapeutic or preventive agents made of sg nucleic acid. The inventors have already shown that the cellular levels of mRNAs encoding Bcl-2 and VEGF, which are promising molecular targets for cancer therapy, can be downregulated under the direction of 5'-half-tRNA-type, 14-nt linear-type, or heptamer-type sg nucleic acid (NPL 1, 4, 17).

From a pharmacological point of view, heptamer-type sg nucleic acid would be the most appropriate for that purpose for the following reasons: heptamers are much easier and cheaper to synthesize than longer sg nucleic acids, and cells can uptake up heptamer-type nucleic acids relatively easily without any stimulating reagents (NPL 18).

CITATION LIST

Patent Literature

PTL 1: Japanese Patent No. 3660718

Non Patent Literatures

NPL 1: Tamura, M., Nashimoto, C., Miyake, N., Daikuhara, Y., Ochi, K. and Nashimoto, M. (2003) Intracellular mRNA cleavage by 3' tRNase under the direction of 2'-O-methylRNA heptamers. Nucleic Acids Res., 31, 4354-4360.

NPL 2: Habu, Y., Miyano-Kurosaki, N., Kitano, M., Endo, Y., Yukita, M., Ohira, S., Takaku, H., Nashimoto, M. and Takaku, H. (2005) Inhibition of HIV-1 gene expression by retroviral vector-mediated small-guide RNAs that direct specific RNA cleavage by tRNase ZL. Nucleic Acids Res., 33, 235-243.

NPL 3: Nakashima, A., Takaku, H., Shibata, H. S., Negishi, Y., Takagi, M., Tamura, M. and Nashimoto, M. (2007) Gene-silencing by the tRNA maturase tRNase ZL under the direction of small guide RNA. Gene Therapy, 14, 78-85.

NPL 4: Elbarbary, R. A., Takaku, H., Tamura, M. and Nashimoto, M. (2009) Inhibition of vascular endothelial growth factor expression by TRUE gene silencing. Biochem. and Biophys. Res. Commun., 379, 924-927.

NPL 5: Nashimoto, M. (1997) Distribution of both lengths and 5' terminal nucleotides of mammalian pre-tRNA 3' trailers reflects properties of 3' processing endoribonuclease. Nucleic Acids Res., 25, 1148-1155.

NPL 6: Takaku, H., Minagawa, A., Masamichi, T. and Nashimoto, M. (2003) A candidate prostate cancer susceptibility gene encodes tRNA 3' processing endoriobonuclease. Nucleic Acids Res., 31, 2272-2278.

NPL 7: Nashimoto, M. (1995) Conversion of mammalian tRNA 3' processing endoribonuclease to four-base-recognizing RNA cutters. Nucleic Acids Res., 23, 3642-3647.

NPL 8: Nashimoto, M. (1996) Specific cleavage of target RNAs from HIV-1 with 5' half tRNA by mammalian tRNA 3' processing endoribonuclease. RNA, 2, 2523-2524.

NPL 9: Nashimoto, M., Geary, S., Tamura, M. and Kasper, R. (1998) RNA heptamers that directs RNA cleavage by mammalian tRNA 3' processing endoribonuclease. Nucleic Acids Res., 26, 2565-2571.

NPL 10: Nashimoto, M. (2000) Anomalous RNA substrates for mammalian tRNA 3' processing endoribonuclease. FEBS Letters, 472, 179-186.

NPL 11: Takaku, H., Minagawa, A., Takagi, M. and Nashimoto, M. (2004) The N-terminal half-domain of the long form of tRNase Z is required for the RNase 65 activity. Nucleic Acids Res., 32, 4429-4438.

NPL 12: Takaku, H., Minagawa, A., Takagi, M. and Nashimoto, M. (2004) A novel four-base-recognizing RNA cutter that can remove the single 3' terminal nucleotides from RNA molecules. Nucleic Acids Res., 32, e91.

NPL 13: Shibata, H. S., Takaku, H., Takagi, M. and Nashimoto, M. (2005) The T loop structure is dispensable for substrate recognition by tRNase ZL. J. Biol. Chem., 280, 22326-22334.

NPL 14: Appasani, K. (2005) RNA interference technology: from basic science to drug development. Cambridge University Press, Cambridge.

NPL 15: Elbarbary, R. A., Takaku, H., Uchiumi, N., Tamiya, H., Abe, M., Takahashi, M., Nishida, H. and Nashimoto, M. (2009) Modulation of gene expression by human cytosolic tRNase ZL through 5'-half-tRNA. PLoS ONE, 4, e5908.

NPL 16: Elbarbary, R. A., Takaku, H., Uchiumi, N., Tamiya, H., Abe, M., Nishida, H. and Nashimoto, M. (2009) Human cytosolic tRNase ZL can downregulate gene expression through miRNA. FEBS Lett., 583, 3241-3246.

NPL 17: Hu, W. and Kavanagh, J. J. (2003) Anticancer therapy targeting the apoptotic pathway. Lancet Oncol., 4, 721-729.

NPL 18: Loke, S. L., Stein, C. A., Zhang X. H., Mori, K., Nakanishi, M., Subasinghe, C., Cohen, J. S. and Neckers, L. M, (1989) Characterization of oligonucleotide transport into living cells. Proc. Natl. Acad. Sci. USA, 86, 3474-3478.

SUMMARY

Technical Problem

The present inventors have shown that heptamer type sg nucleic acids effectively suppress expression of genes associated with cancer. For cancer treatment, however, improved effects are needed that can reliably kill cancer cells.

It is accordingly an object of the present invention to provide novel heptamer-type sg nucleic acids that can reliably induce apoptosis of human leukemia cells.

Solution to Problem

The present inventors searched numerous heptamer-type small guide nucleic acids ($(A, U, G, C)^7=16,384$), and found fifteen heptamer-type small guide nucleic acids that induce apoptosis of human leukemia cells without having any adverse effects on survival of normal cells. The present invention has been completed on the basis of this finding. Specifically, the present invention provides solutions to the foregoing problems, as follows.

(1) A heptamer-type small guide nucleic acid inducing apoptosis of human leukemia cells, which comprises any of the 7-base sequences of SEQ ID NOS: 1 to 15, and.

(2) The heptamer-type small guide nucleic acid of (1), wherein the apoptosis kills 85% or more of the human leukemia cells in 3 days.

(3) A leukemia therapeutic agent that comprises one or more of the heptamer-type small guide nucleic acid of (1) or (2) as an active ingredient.

Advantageous Effects of Invention

The heptamer-type sg nucleic acids of the present invention induce apoptosis of human leukemia cells (specifically, apoptosis of 85% or more of human leukemia cells in 3 days). This provides an effective means of leukemia treatment.

DESCRIPTION OF EMBODIMENTS

The heptamer-type sg nucleic acid of the present invention is any of the 15 heptamer-type sg nucleic acids presented in Table 1.

TABLE 1

| SEQ ID NO | Sequence 5'-------3' | Name |
|---|---|---|
| 1 | GGGCCAG | Hep1(bcl-2) |
| 2 | GGGGGCG | Hep2(bcl-2) |
| 3 | GGGUCCU | Hep5(IRF4) |
| 4 | CAGCUCG | Hep1(MYC) |
| 5 | GCAGCUC | Hep3(MYC) |
| 6 | GCUGCUG | Hep5(MYC) |
| 7 | CCGGGGC | Hep2(PKCb) |
| 8 | AUCUUCA | Hep8(FGFR3) |
| 9 | CACCAGC | Hep9(FGFR3) |
| 10 | GCUCUGC | Hep5(PRAME) |
| 11 | UCUUUCC | Hep1(HAGE) |
| 12 | UAUAUUU | Hep2(HAGE) |
| 13 | GCAUGCG | Hep(YW) |
| 14 | UCCAGGU | Hep6(PRAME) |
| 15 | CUGCUUU | Hep7(WT1) |

Table 1 shows the sequence of each sgRNA. These fifteen heptamer-type sgRNAs were selected from $(A, U, G, C)^7=16,384$ oligonucleotides on the basis of the confirmed effect of inducing apoptosis of human leukemia cells. A cleavage target gene mRNA can be envisaged from these nucleotide sequences. However, the target gene is not necessarily a single gene. mRNAs with a 7-nt sequence that anneals to any of the oligonucleotides may originate from more than one gene, including unknown genes. As such, the symbols used in the parentheses under the heading "Name" in Table 1 each represent an example of a gene that is transcribes into a target mRNA cleaved by the heptamer-type sgRNA.

The heptamer-type sg nucleic acids can cause cell death (apoptosis) in 85% or more of human leukemia cells in 3 days, as described in Examples.

The heptamer-type sg nucleic acids may be produced, for example, using known chemical synthesis methods, or enzymatic transcription methods. Examples of the known chemical synthesis methods include the phosphoramidite method, the phosphorothioate method, and the phosphotriester method. For example, the ABI3900 high throughput nucleic acid synthesizer (Applied Biosystems), the NTS H-6 nucleic acid synthesizer (Nihon Techno Service Co., Ltd.), and the Oligoilot 10 nucleic acid synthesizer (GE Healthcare) may be used for the synthesis. As an example of the enzymatic transcription methods, a transcription method may be used that uses an RNA polymerase, such as T7, T3, and SP6 RNA polymerases, using a template plasmid or DNA having a base sequence of interest. The heptamer-type sg nucleic acid produced by the chemical synthesis or transcription is purified by HPLC or the like. For example, in HPLC purification, the heptamer-type sg nucleic acid is eluted from the column using a mixed solution of triethylammonium acetate (TEAA) or hexylammonium acetate (HAA) and acetonitrile. The eluate is then dialyzed for 10 hours with distilled water used in 1,000 times the elution volume. The resulting solution is freeze dried, and cryogenically preserved until use. For use, the heptamer-type sg nucleic acid is dissolved in distilled water to make the final concentration about 100 µM.

Any nucleic acid may be used for the heptamer-type sg nucleic acids of the present invention, provided that it is a molecule formed by polymerization of a nucleotide or a functionally equivalent molecule thereof. Examples of the nucleotide include a ribonucleotide polymer RNA, a deoxyribonucleotide polymer DNA, a mixed polymer of RNA and DNA, and a nucleotide polymer containing a nucleotide analog. Particularly preferred is RNA.

Examples of the nucleotide analog include molecules produced by modifying ribonucleotides, deoxyribonucleotides, or RNAs or DNAs to provide improved or more stable nuclease resistance, improved affinity to complementary strand nucleic acids, improved cell permeability, or better visualization compared to RNAs or DNAs. Specific examples include sugar-modified nucleotide analogs, and phosphodiester bond-modified nucleotide analogs.

The sugar-modified nucleotide analogs may be any molecules, as long as the chemical structure of the nucleotide sugar has the chemical structure of a substance added or substituted with respect to the sugar either in part or as a whole. Examples include nucleotide analogs substituted with 2'-O-methylribose, nucleotide analogs substituted with 2'-O-propylribose, nucleotide analogs substituted with 2'-methoxyethoxyribose, nucleotide analogs substituted with 2'-O-methoxyethylribose, nucleotide analogs substituted with 2'-O-[2-(guanidium)ethyl]ribose, nucleotide analogs substituted with 2'-O-fluororibose, bridged synthetic nucleic acids (Bridged Nucleic Acids; BNAs) having two cyclic structures after introduction of a bridged structure to the sugar moiety, more specifically locked synthetic nucleic acids (Locked Nucleic Acids; LNAs) having a bridge connecting the 2'-position oxygen atom and the 4'-position carbon atom via methylene, and ethylene bridged synthetic nucleic acid (ethylene bridged nucleic acids; ENAs) [Nucleic Acid Research, 32, e175 (2004)]. Other examples include peptide nucleic acids (PNAs) [Acc. Chem. Res., 32, 624 (1999)], oxypeptide nucleic acids (OPNAs) [J. Am. Chem. Soc., 123, 4653 (2001)], and peptide ribonucleic acids (PRNAs) [J. Am. Chem. Soc., 122, 6900 (2000)].

The phosphodiester bond-modified nucleotide analogs may be any molecules, as long as the chemical structure of the nucleotide phosphodiester bond has a substance added or substituted with respect to the phosphodiester bond either in part or as a whole. Examples include nucleotide analogs having a substituted phosphorothioate bond, and nucleotide analogs having a substituted N3'-P5' phosphoramidate bond [Cell Engineering, 16, 1463-1473 (1997)] [RNAi Method and Antisense method, Kodansha (2005)].

Further, the nucleotide analog may be one in which the atoms (for example, hydrogen atom, oxygen atom), or the functional groups (for example, hydroxyl group, amino group) in the base moiety, the ribose moiety, and the phosphodiester bond moiety of the nucleic acid are substituted by other atoms (for example, hydrogen atom, sulfur atom), functional groups (for example, amino group), or alkyl groups of 1 to 6 carbon atoms, or protected by protecting groups (for example, methyl group, or acyl group). Molecules obtained by addition of other chemical substances, for example, such as lipids, phospholipids, phenazine, folate, phenanthridine, anthraquinone, acridine, fluorescein, rhodamine, coumalin, and dyes to nucleic acid also may be used.

Examples of the molecules obtained by addition of other chemical substances to nucleic acid include 5'-polyamine adduct derivatives, cholesterol adduct derivatives, steroid adduct derivatives, bile acid adduct derivatives, vitamin adduct derivatives, Cy5 adduct derivatives, Cy3 adduct derivatives, 6-FAM adduct derivatives, and biotin adduct derivatives.

The cancer therapeutic agent of the present invention contains one or more heptamer-type sg nucleic acids of the present invention. Two or more heptamer-type sg nucleic acids may be used in any combination. Specifically, the heptamer-type sg nucleic acids of the present invention can individually induce apoptosis of leukemia cells through TRUE gene silencing of gene mRNA necessary for survival of leukemia cells. In this case, the heptamer-type sg nucleic acids cleave different target gene mRNAs, or cleave the same target gene mRNA at different sites. That is, combining two or more heptamer-type sg nucleic acids allows for TRUE gene silencing of two or more gene mRNAs necessary for survival of leukemia cells, and can effectively induce apoptosis of leukemia cells. It is also possible to effectively induce apoptosis of leukemia cells by combining heptamer-type sg nucleic acids that cleave the same target gene mRNA at different sites.

The heptamer-type sg nucleic acids may be made into a preparation alone. More desirably, the heptamer-type sg nucleic acids are typically mixed with one or more pharmaceutically acceptable carriers, and administered as a pharmaceutical preparation produced using any method well known in the field of pharmaceutics.

It is desirable to use a administration route most effective for the treatment, and the route may be, for example, an oral administration route, or a parenteral administration route such as buccal administration, airway administration, rectal administration, subcutaneous administration, intramuscular administration, and intravenous administration. Preferred is an intravenous administration.

Examples of preparations suitable for oral administration include an emulsion, a syrup, a capsule formulation, a tablet, a powder, and a granule. Liquid preparations such as an emulsion and a syrup may be produced with additives such as water, sugars (e.g., sucrose, sorbitol, and fructose), glycols (e.g., polyethylene glycol, and propylene glycol), oils (e.g., sesame oil, olive oil, and soybean oil), preservatives (e.g., p-hydroxybenzoic acid esters), and flavors (e.g., strawberry flavor, and peppermint flavor). Preparations such as a capsule formulation, a tablet, a powder, and a granule may be produced with additives such as excipients (e.g., lactose, glucose, sucrose, and mannitol), disintegrants (e.g., starch, and sodium alginate), lubricants (e.g., magnesium stearate, and talc), binders (e.g., polyvinyl alcohol, hydroxypropyl cellulose, and gelatin), surfactants such as fatty acid ester), and plasticizers (e.g., glycerine).

Examples of preparations suitable for parenteral administration include injections, suppositories, and aerosolized agents. The injections may be prepared using carriers such as a salt solution, a glucose solution, and a mixture of these. The suppositories may be prepared using carriers such as a cacao butter, a hydrogenated fat, and a carboxylic acid. The aerosolized agents may be prepared using carriers that do not stimulate the mouth and airway mucosa of a recipient, and that disperse the active ingredient in the form of fine particles to facilitate absorption.

Specific examples of the carriers include lactose, and glycerine. The preparations may be, for example, in the form of an aerosol, a dry powder, or the like as may be decided according to the properties of the nucleic acid used in the present invention, and the properties of the carrier used. The same components exemplified for the oral administration additives also may be used for the parenterally administered form.

The dose and the dosing intervals vary according to such factors as the intended therapeutic effect, the administration method, the duration of therapy, and the age and body weight. Typically, the dose is 10 µg/kg/day to 20 mg/kg/day for adults.

The present invention is described below in greater detail using Examples. It should be noted, however, that the present invention is not limited by the following Examples.

Example 1

(1) Methods
(1-1) Synthesis of Heptamer-Type sgRNA

The fifteen heptamer-type sgRNAs (SEQ ID NOS: 1-15) shown in Table 1 were synthesized using a chemical synthesizer.

The sgRNAs are phosphorylated at the 5' and 3' ends, and 2'-O-methylated. Each synthesized sgRNA was purified by HPLC. For purification, the synthesized sgRNA was eluted from the column using a mixed solution of hexylammonium acetate (HAA) and acetonitrile. The eluate was then dialyzed for 10 hours with distilled water used in 1,000 times the elution volume. The resulting solution was freeze dried, and cryogenically preserved until use. For use, the sg RNA was dissolved in distilled water to make the final concentration about 100 µM. The remaining solution was cryogenically preserved.

(1-2) MTT Assay

Each sgRNA (final concentration 1 µM) was added to a 96-well culture plate containing human cancer cell lines (1,000 cells/100 µl medium), without using a reagent for the delivery of the sgRNA into the cells. The cells were then cultured in a 37° C. $CO_2$ incubator. After 72 hours, an MTT reagent (Tetracolor One 6 µl, Seikagaku Biobusiness) was added, and a 450 nm absorbance was measured with a spectrophotometer after 3 hours and 6 hours to quantify the viable cells (displayed as a triplicate mean value). Leukemia cells HL60, and myeloma cells KMM1 and RPMI-8226 were used as the human cancer cell lines, and the viable cell count was compared with that of an sgRNA non-administered group. As controls, each sgRNA was introduced to normal cells HEK293, and the same MTT assay was performed.

(1-3) Flow Cytometry Experiment

The sgRNA (final concentration 1 µM) was added to a 96-well culture plate containing human cancer cell lines (1,000 cells/100 µl medium), without using a reagent for the delivery of the sgRNA into the cells. The cells were then cultured in a 37° C. $CO_2$ incubator. After 72 hours, the cells were stained with phycoerythrin-conjugated Annexin V (BD Pharmingen) and 7-AAD (Sigma) at room temperature for 15 minutes, and analyzed with a flow cytometer (FACSCalibur).

(1-4) Mouse Xenograft Experiment $2 \times 10^6$ human leukemia cells HL60 were subcutaneously transplanted into immunodeficient nude mice with an extracellular matrix. Each heptamer-type sgRNA (100 µM) was continuously administered to the transplantation site in a dose of 10 µl, once each day for 5 days, and the tumor volume was measured every day. The mice were euthanized upon the tumor volume reaching 1,500 mm³. The experiment was conducted with groups of 6 to 8 mice, and the difference between the median value of the survival time of each sgRNA administered group and the median value of the survival time of the non-administered group (or a group administered with the ineffective heptamer-type sgRNA) was calculated as the extended lifetime due to the heptamer-type sgRNA.

(2) Results
(2-1) MTT Assay

The results are presented in Table 2. The heptamer-type sgRNAs of SEQ ID NOS: 1-15 killed 85% or more of the human leukemia cell line HL60 in 3 days. The heptamer-type sgRNAs of SEQ ID NOS: 8 and 9 killed 75% or more of the human leukemia cells and the human myeloma cell lines KMM1 and RPMI-8226 in 3 days. The heptamer-type sg nucleic acids of SEQ ID NOS: 6 and 12 killed 72% of the myeloma cell line KMM1 in 3 days. The heptamer-type sg nucleic acid of SEQ ID NO: 7 killed 75% of the myeloma cell line RPMI-8226 in 3 days. The heptamer-type sg nucleic acids having the apoptosis inducing effect against KMM1 cells and RPMI-8226 cells can thus be used also for treatment of human myeloma. The death rate of the normal cells HEK293 was 0% in all the heptamer-type sg nucleic acids,

TABLE 2

| SEQ ID NO | Sequence 5'-3' | Name | MTT assay (Percentage reduction of viable cells) | | | Mouse xenograft experiment (Extended lifetime) |
|---|---|---|---|---|---|---|
| | | | HL60 | KMM1 | RPMI | |
| 1 | GGGCCAG | Hep1(bcl-2) | 88% | 0% | 18% | HL60 (+22 days) |
| 2 | GGGGGCG | Hep2(bcl-2) | 99% | 24% | 69% | HL60 (+19 days) |
| 3 | GGGUCCU | Hep5(IRF4) | 86% | 69% | 6% | |
| 4 | CAGCUCG | Hep1(MYC) | 90% | 56% | 16% | |
| 5 | GCAGCUC | Hep3(MYC) | 90% | 67% | 2% | |
| 6 | GCUGCUG | Hep5(MYC) | 86% | 72% | 0% | |
| 7 | CCGGGGC | Hep2(PKCb) | 93% | 48% | 75% | |
| 8 | AUCUUCA | Hep8(FGFR3) | 87% | 78% | 76% | HL60 (+10 days) |
| 9 | CACCAGC | Hep9(FGFR3) | 95% | 79% | 76% | HL60 |

TABLE 2 -continued

| SEQ ID NO | Sequence 5'-3' | Name | MTT assay (Percentage reduction of viable cells) | | | Mouse xenograft experiment (Extended lifetime) |
|---|---|---|---|---|---|---|
| | | | HL60 | KMM1 | RPMI | (+6 days) |
| 10 | GCUCUGC | Hep5(PRAME) | 94% | 17% | 54% | |
| 11 | UCUUUCC | Hep1(HAGE) | 91% | 61% | 5% | |
| 12 | UAUAUUU | Hep2(HAGE) | 94% | 72% | 5% | |
| 13 | GCAUGCG | Hep(YW) | 96% | 59% | 0% | |
| 14 | UCCAGGU | Hep6(PRAME) | 95% | 15% | 10% | |
| 15 | CUGCUUU | Hep7(WT1) | 98% | 24% | 46% | |

(2-2) Flow Cytometry Experiment

Figure 1:
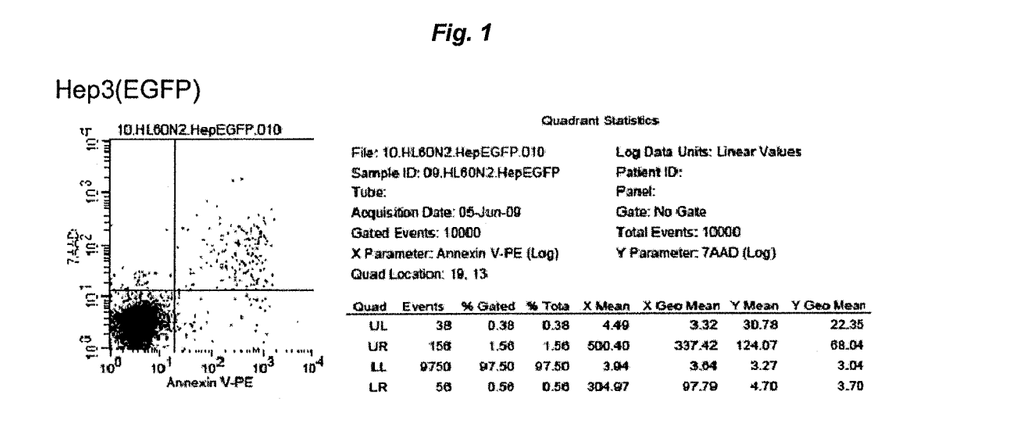
FIG. 1 represents the result of a flow cytometry experiment in which an ineffective sgRNA [Hep3(EGFP)] was introduced into HL60 cells.
Figure 2:
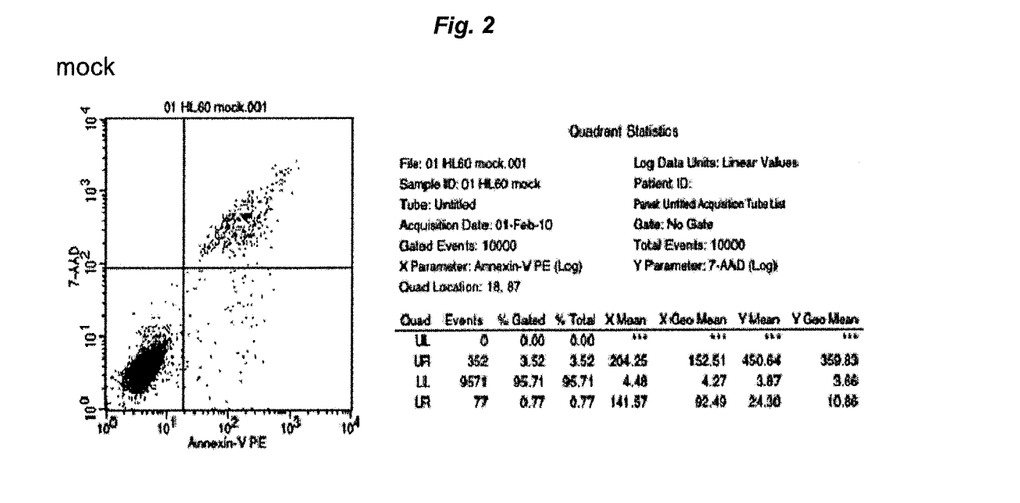
FIG. 2 represents the result of a flow cytometry experiment in which sgRNA was not added to HL60 cells (mock).
Figure 3:
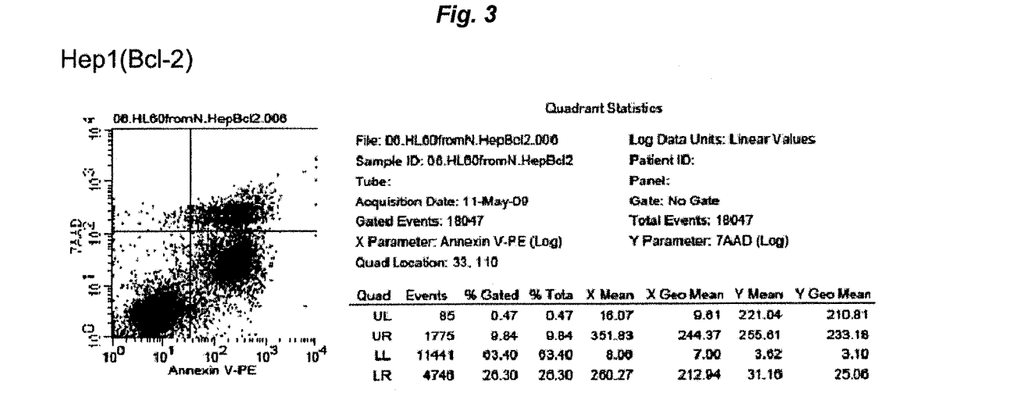
FIG. 3 represents the result of a flow cytometry experiment in which Hep1(Bcl-2) (SEQ ID NO: 1) was introduced into HL60 cells.
Figure 4:
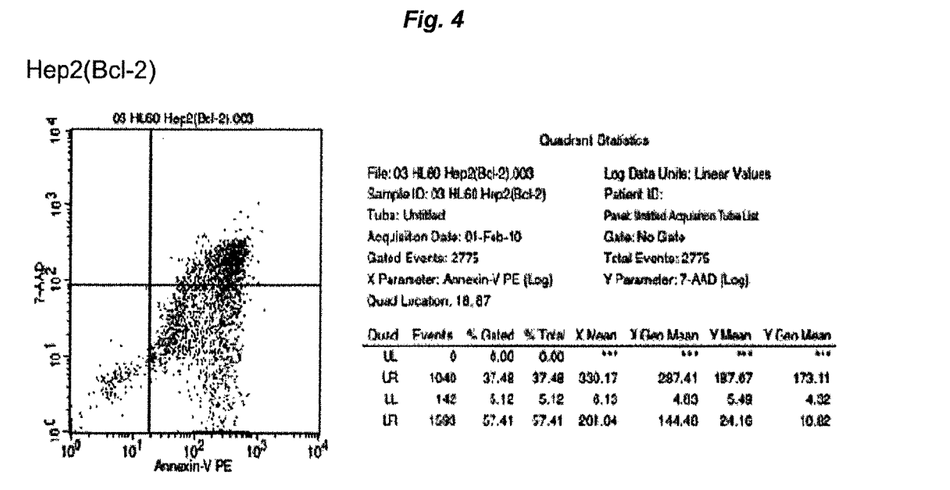
FIG. 4 represents the result of a flow cytometry experiment in which Hep2(Bcl-2) (SEQ ID NO: 2) was introduced into HL60 cells.
Figure 5:
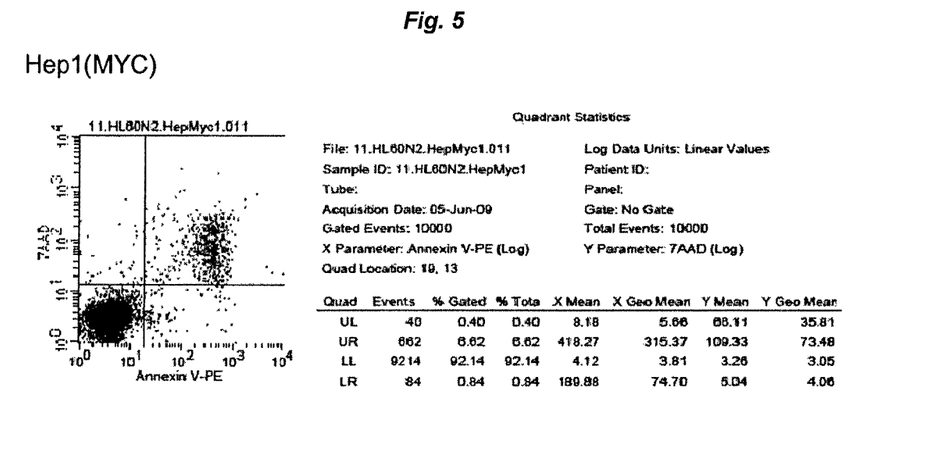
FIG. 5 represents the result of a flow cytometry experiment in which Hep1(MYC) (SEQ ID NO: 4) was introduced into HL60 cells.
Figure 6:
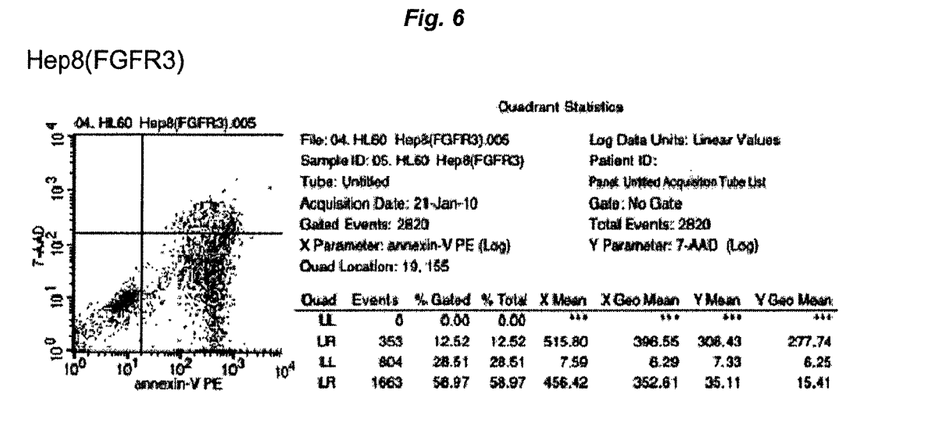
FIG. 6 represents the result of a flow cytometry experiment in which Hep8(FGFR3) (SEQ ID NO: 8) was introduced into HL60 cells.
Figure 7:
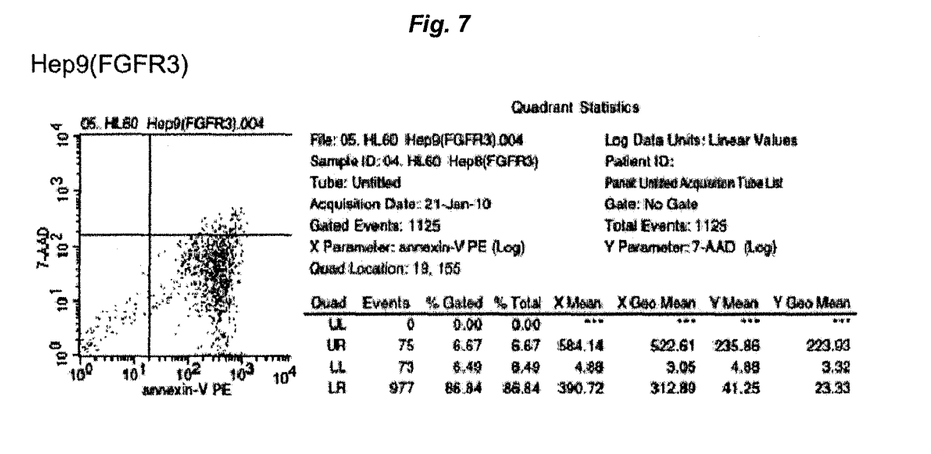
FIG. 7 represents the result of a flow cytometry experiment in which Hep9(FGFR3) (SEQ ID NO: 9) was introduced into HL60 cells.
Figure 8:
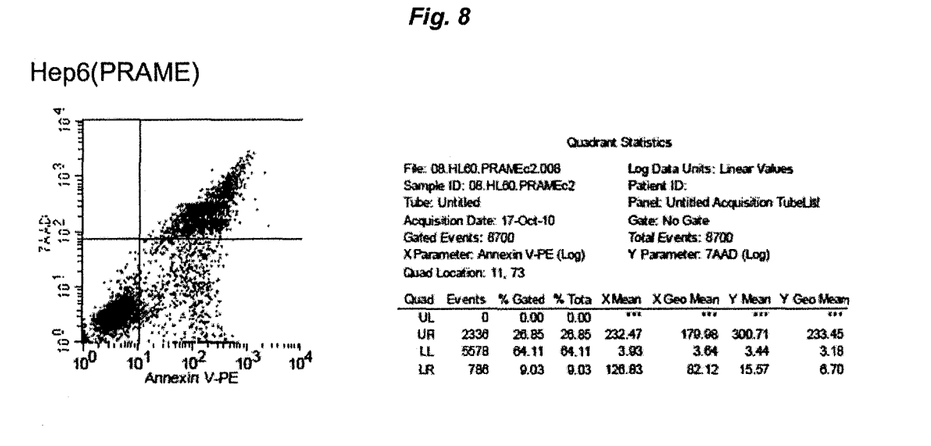
FIG. 8 represents the result of a flow cytometry experiment in which Hep6(PRAME) (SEQ ID NO: 14) was introduced into HL60 cells.
Figure 9:
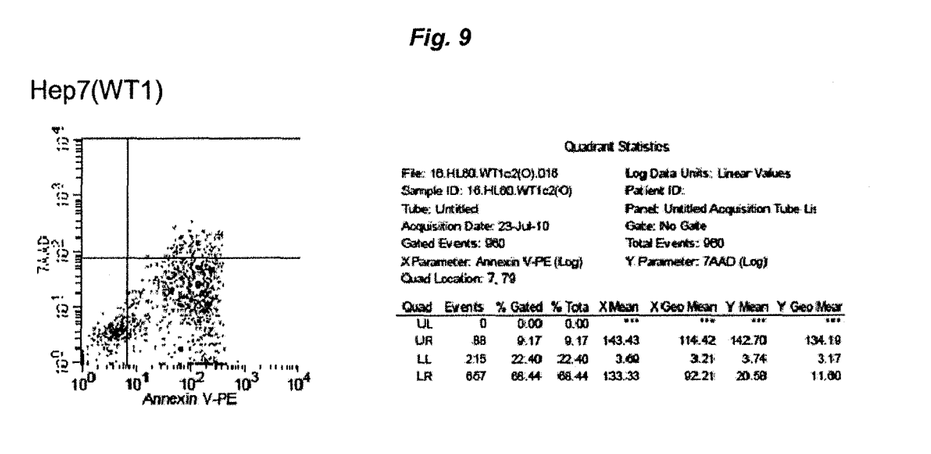
FIG. 9 represents the result of a flow cytometry experiment in which Hep7(WT1) (SEQ ID NO: 15) was introduced into HL60 cells.

The results are presented in FIGS. 1 to 9. It was confirmed that the heptamer-type sgRNAs tested were able to induce apoptosis in a much greater number of cells compared to the ineffective heptamer-type sgRNA [(Hep3(EGFP))] and no sgRNA (mock).

(2-3) Mouse Xenograft Experiment

The results are presented in Table 2. The heptamer-type sgRNAs tested extended the lifetime of the HL60 cell transplanted mice by at least 6 days, and as long as 22 days.

It was confirmed from these results that the heptamer-type sg nucleic acids of the present invention were able to effectively induce apoptosis of human leukemia cells, and extend the lifetime of animal individuals with leukemia cells through the induced apoptosis.

INDUSTRIAL APPLICABILITY

The present invention provides an effective treatment for human leukemia.

The invention claimed is:

1. A leukemia therapeutic agent, which comprises one or more of a small guide RNA consisting of a sequence selected from SEQ ID NOS: 1, 2, 3, 4, 7, 8, 10, 11, 12, 13 or 15 as an active ingredient,
wherein one or more of the small guide RNA is phosphorylated at the 5' and 3' ends, and is 2'-O-methylated.

2. A composition comprising one or more of a small guide RNA consisting of a sequence selected from SEQ ID NOS: 1, 2, 3, 4, 7, 8, 10, 11, 12, 13 or 15 and a pharmaceutically acceptable carrier,
wherein one or more of the small guide RNA is phosphorylated at the 5' and 3' ends, and is 2'-O-methylated.

* * * * *

SEQUENCE LISTING

<160> NUMBER OF SEQ ID NOS: 15

<210> SEQ ID NO 1
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 1 gggccag                                                                7

<210> SEQ ID NO 2
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 2 gggggcg                                                                7

<210> SEQ ID NO 3
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 3 ggguccu                                                                7

<210> SEQ ID NO 4
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 4 cagcucg                                                                7

```
<210> SEQ ID NO 5
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 5 gcagcuc                                                                    7

<210> SEQ ID NO 6
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 6 gcugcug                                                                    7

<210> SEQ ID NO 7
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 7 ccggggc                                                                    7

<210> SEQ ID NO 8
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 8 aucuuca                                                                    7

<210> SEQ ID NO 9
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 9 caccagc                                                                    7

<210> SEQ ID NO 10
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 10 gcucugc                                                                    7
```

```
<210> SEQ ID NO 11
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 11 ucuuucc                                                                    7

<210> SEQ ID NO 12
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 12 uauauuu                                                                    7

<210> SEQ ID NO 13
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 13 gcaugcg                                                                    7

<210> SEQ ID NO 14
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 14 uccaggu                                                                    7

<210> SEQ ID NO 15
<211> LENGTH: 7
<212> TYPE: RNA
<213> ORGANISM: Artificial
<220> FEATURE:
<223> OTHER INFORMATION: Description of artificial sequence: Synthetic
      oligonucleotide

<400> SEQUENCE: 15 cugcuuu                                                                    7
```